United States Patent
Kheradpir et al.

(10) Patent No.: US 11,020,187 B2
(45) Date of Patent: Jun. 1, 2021

(54) TRACKED SUCTION TOOL

(71) Applicant: SYNAPTIVE MEDICAL INC., Toronto (CA)

(72) Inventors: Leila Kheradpir, Toronto (CA); Kyle Richard Dupont, Toronto (CA); Jakub Jankowski, Toronto (CA)

(73) Assignee: SYNAPTIVE MEDICAL INC., Toronto (CA)

( * ) Notice: Subject to any disclaimer, the term of this patent is extended or adjusted under 35 U.S.C. 154(b) by 549 days.

(21) Appl. No.: 15/732,113

(22) Filed: Sep. 21, 2017

(65) Prior Publication Data
US 2019/0083179 A1 Mar. 21, 2019

(51) Int. Cl.
*A61B 34/20* (2016.01)
*A61B 5/06* (2006.01)
(Continued)

(52) U.S. Cl.
CPC ............ *A61B 34/20* (2016.02); *A61B 5/0077* (2013.01); *A61B 5/061* (2013.01); *A61B 5/064* (2013.01);
(Continued)

(58) Field of Classification Search
CPC ... A61M 1/0086; A61M 1/0047; A61B 34/20; A61B 90/36; A61B 90/39; A61B 5/0077;
(Continued)

(56) References Cited

U.S. PATENT DOCUMENTS

| RE43,526 E * | 7/2012 | Morrison ........... A61B 17/7091 |
| | | 606/86 A |
| 2002/0107457 A1* | 8/2002 | Francese ............ A61B 10/0266 |
| | | 600/564 |

(Continued)

FOREIGN PATENT DOCUMENTS

| WO | 95/13105 A2 | 5/1995 |
| WO | 2016/116843 A1 | 7/2016 |
| WO | 2017/051224 A1 | 3/2017 |

OTHER PUBLICATIONS

Search report issued by the Intellectual Property Office of the United Kingdom in relation to corresponding GB application No. GB1815354.4 dated May 7, 2019, 5 pgs.

*Primary Examiner* — Amelie R Davis
*Assistant Examiner* — John Denny Li

(57) ABSTRACT

A device and method is provided for a trackable suction tool for surgical use. The tracked suction tool includes a tubular handle with a main tube and an entrance tube extending from the main tube, a flattened section of the main tube with a suction-regulating orifice, a tip connected to the main tube distal end and a tracking mechanism connected to a handle proximal end. A method is provided for tracking the position of a tracked suction device including attaching a tip to a handle in one of a plurality of fixed positions, attaching a tracking mechanism to the handle in one of a plurality of fixed positions, calibrating the position of the tip with a positional tracking system using the tracking mechanism, (Continued)

positioning the tracking markers in view of the positional tracking system and tracking a position of the distal end of the tip of the suction device.

8 Claims, 9 Drawing Sheets

(51) Int. Cl.
    *A61B 90/00*     (2016.01)
    *A61M 1/00*     (2006.01)
    *A61B 5/00*     (2006.01)
    *A61B 17/00*     (2006.01)
    *A61B 5/1495*     (2006.01)

(52) U.S. Cl.
CPC .............. *A61B 90/36* (2016.02); *A61B 90/39* (2016.02); *A61M 1/0047* (2013.01); *A61M 1/0086* (2014.02); *A61B 5/1495* (2013.01); *A61B 2017/00477* (2013.01); *A61B 2017/00725* (2013.01); *A61B 2034/207* (2016.02); *A61B 2034/2051* (2016.02); *A61B 2034/2055* (2016.02); *A61B 2090/3945* (2016.02); *A61B 2090/3983* (2016.02)

(58) Field of Classification Search
CPC ......... A61B 5/061; A61B 5/64; A61B 5/1495; A61B 2034/2051; A61B 2034/2055; A61B 2034/207; A61B 2090/3945; A61B 2090/3983; A61B 2017/00477; A61B 2017/00725

See application file for complete search history.

(56) References Cited

U.S. PATENT DOCUMENTS

| | | | |
|---|---|---|---|
| 2005/0113659 A1 | 5/2005 | Pothier | |
| 2005/0245899 A1 | 11/2005 | Swisher | |
| 2005/0260059 A1* | 11/2005 | Lees | F16B 39/16 411/412 |
| 2006/0241627 A1* | 10/2006 | Reo | A61B 17/16 606/79 |
| 2008/0051768 A1 | 2/2008 | Stumpf | |
| 2009/0099445 A1 | 4/2009 | Burger | |
| 2013/0064427 A1* | 3/2013 | Picard | G01S 5/163 382/103 |
| 2014/0005653 A1* | 1/2014 | Shelton, IV | A61B 34/70 606/33 |
| 2014/0117059 A1* | 5/2014 | Piety | B25B 15/008 224/191 |
| 2014/0276004 A1 | 9/2014 | Strupeck et al. | |
| 2018/0214217 A1* | 8/2018 | Rodriguez | A61B 5/062 |
| 2018/0368703 A1* | 12/2018 | Franjic | A61B 5/065 |

* cited by examiner

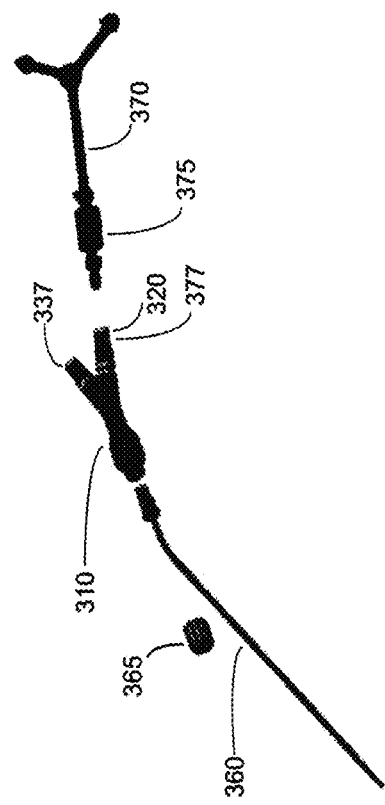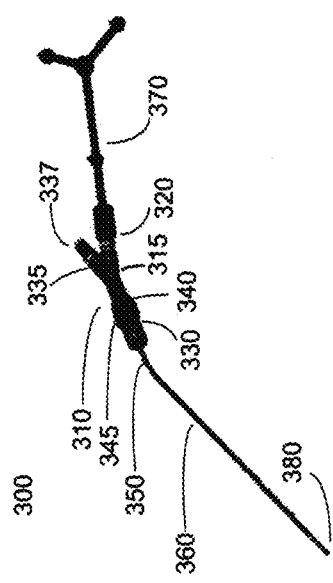
FIG. 3

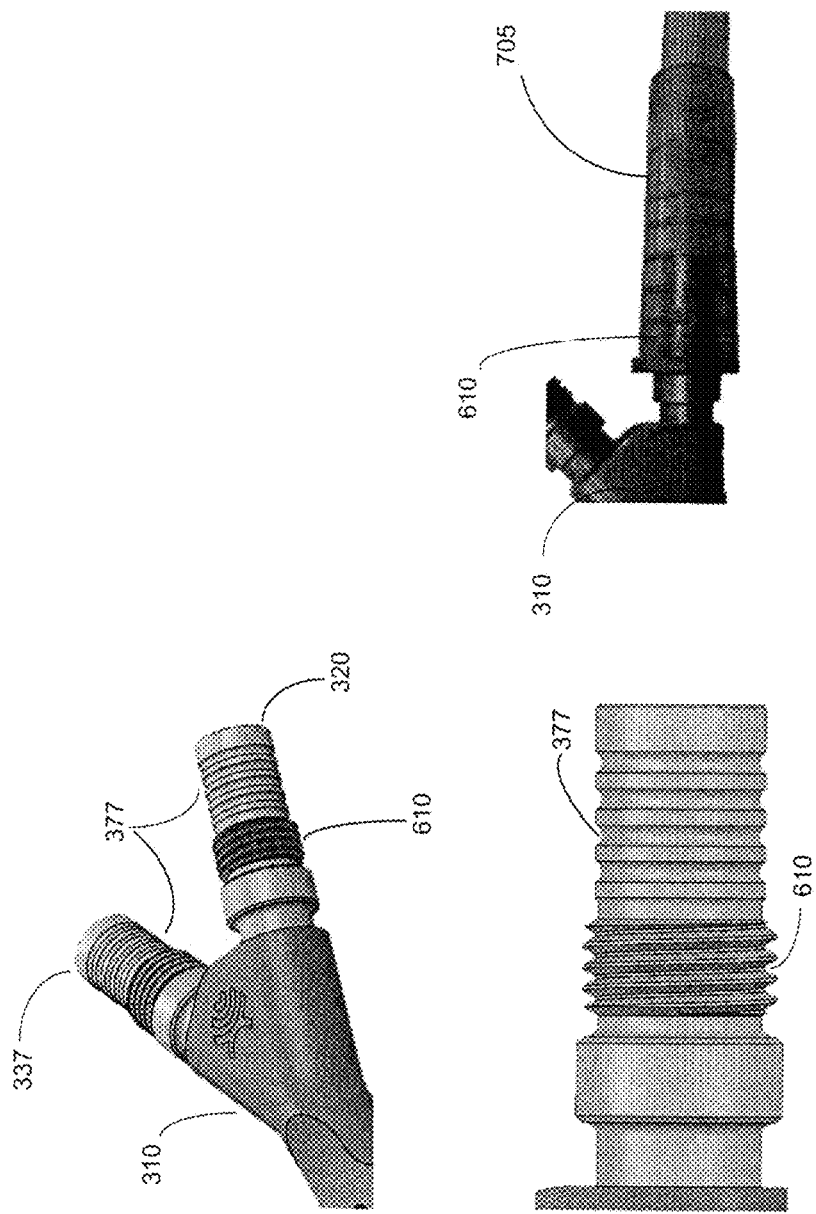

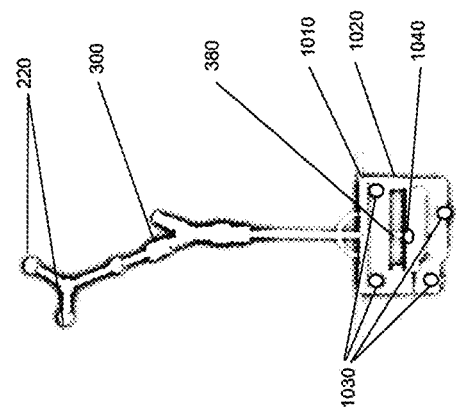
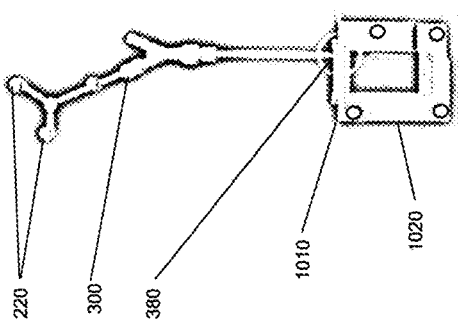
FIG. 10

TRACKED SUCTION TOOL

TECHNICAL FIELD

The present disclosure relates to image guided medical procedures using surgical instrument tracking and more specifically to a tracked suction tool.

BACKGROUND

Surgical procedures have been greatly assisted by the implementation of navigation systems. Navigation systems assist in surgery by providing previously acquired imaging information, such as magnetic resonance imaging, during surgery to visualize tissue morphology and locate target areas. Navigation systems may also be used to track surgical instruments and their location within the tissue during surgery, typically incorporating information from previously acquired imaging data.

As an example, minimally invasive brain surgery may incorporate navigation systems to map a target area for surgical resection and access the target area with minimal damage to healthy brain tissue. Corridor-based or port-based surgery is a minimally invasive neurosurgical procedure allowing a surgeon to perform a surgical procedure involving tumor resection in which the residual tumor remaining after is minimized, while also minimizing the trauma to the intact white and grey matter of the brain. In such procedures, trauma may occur, for example, due to contact with the access port, stress to the brain matter, unintentional impact with surgical devices, and/or accidental resection of healthy tissue.

One aspect in minimizing trauma to intact brain matter is to track the location of surgical tools within the tissue by providing the surgical tool with a tracking device. By tracking a surgical tool, its insertion can be guided within the tissue with minimal impact to healthy tissue and the tool can be positioned correctly to serve its purpose. The tool may be tracked by overlaying a map of its position over a previously acquired or real-time imaging of the tissue. Likewise, other navigated procedures, such as spine, ENT (ear nose throat), orthopedic and cardiac procedures benefit from providing surgical tools with a tracking device.

A navigation system typically includes a tracking device or object marker on the surgical tool and a detector to detect the position of the tracking device. In optical navigation systems, object markers can be light emitting diodes (LEDs), reflective stickers, unique structures and patterns or glass spheres, which utilize optical detectors. Alternatively, object markers can utilize electromagnetic (EM) or radio frequency (RF) signals, which are detected by antennas. Optical detectors require a line-of-sight between the object marker and detector during operation, but are not subject to noise and distortion from environmental influences that electrical detection and emission systems are subject to.

In some cases, it can be difficult to incorporate a tracking device on a surgical instrument, especially instruments with flexible portions or with multiple configurations. For example, if the tracking device is positioned in a handle or proximal region of the instrument and the distal tip moves or is moved relative to the handle, the distal tip can no longer be accurately tracked. Electromagnetic navigation systems have partly overcome the difficulty of tracking flexible tips and multiple configurations by using a flexible membrane over the tip to connect the distal tracking device with the system on the handle. However, this does not overcome the problem of multiple configurations in which the tip is swiveled about the handle or when the tip is exchangeable.

An important surgical tool is a suction device, which can be used for tissue retention, resection and removal of fluids. A suction device typically includes a handle portion and tip portion. The tip portion can be any one of multiple configurations, such as different lengths, angles and diameters, and may be removable so it can be swapped out to provide the most appropriate configuration for the surgical procedure. The multiple configurations of the tip present challenges to tracking the distal end of the tip through a tracking device on the handle, because the relative positions of the distal end of the tip and handle are different for each configuration. The present disclosure attempts to solve this problem to provide a suction device that is trackable over multiple configurations and exchangeable tips.

SUMMARY

An object of the present disclosure is to provide methods and devices for tracking suction tools using surgical navigation systems or positional tracking systems. Thus by one broad aspect of the present disclosure, a tracked suction device is provided for use in a medical procedure comprising: an elongated tubular handle with a central passage, a main tube having a first proximal end, a distal end, and a flattened section with a suction-regulating orifice communicating with the central passage, and an entrance tube extending from the main tube having a second proximal end; an elongated tip, having a hollow tubular body, a tip distal end, and a tip proximal end detachably connected to the main tube distal end; and a tracking mechanism detachably connected to the handle first or second proximal end, for tracking the tip distal end, wherein the flattened section of the main tube lies in a plane defined by the main tube and the entrance tube, and the handle first and second proximal ends may be connected to the tracking mechanism or a suction hose.

By another broad aspect of the present disclosure, a method is provided for tracking the position of a tracked suction device in a medical procedure, comprising: attaching a tip to a handle in one of a plurality of fixed positions; attaching a tracking mechanism to the handle in one of a plurality of fixed positions; calibrating the position of the tip distal end with a positional tracking system using the tracking mechanism; positioning the tracking markers of the tracked suction device in view of the tracking source (optical camera) of the positional tracking system to be tracked; and tracking a position of the distal end of the tip of the suction device.

A further understanding of the functional and advantageous aspects of the disclosure can be realized by reference to the following detailed description and drawings.

BRIEF DESCRIPTION OF THE DRAWINGS

FIG. 3 illustrates an assembled and exploded view of an exemplary tracked suction device in accordance with example embodiments of the present disclosure.

FIG. 6 illustrates a perspective and side view of attachment fittings for attaching a handle to a suction hose and tracking device in accordance with example embodiments of the present disclosure.

FIG. 7 illustrates a suction hose connection to a handle in accordance with example embodiments of the present disclosure.

FIG. 10 illustrates a perspective view of a tracked instrument shown in FIG. 3 inserted into a calibration apparatus in accordance with example embodiments of the present disclosure.

DETAILED DESCRIPTION

Figure 1:
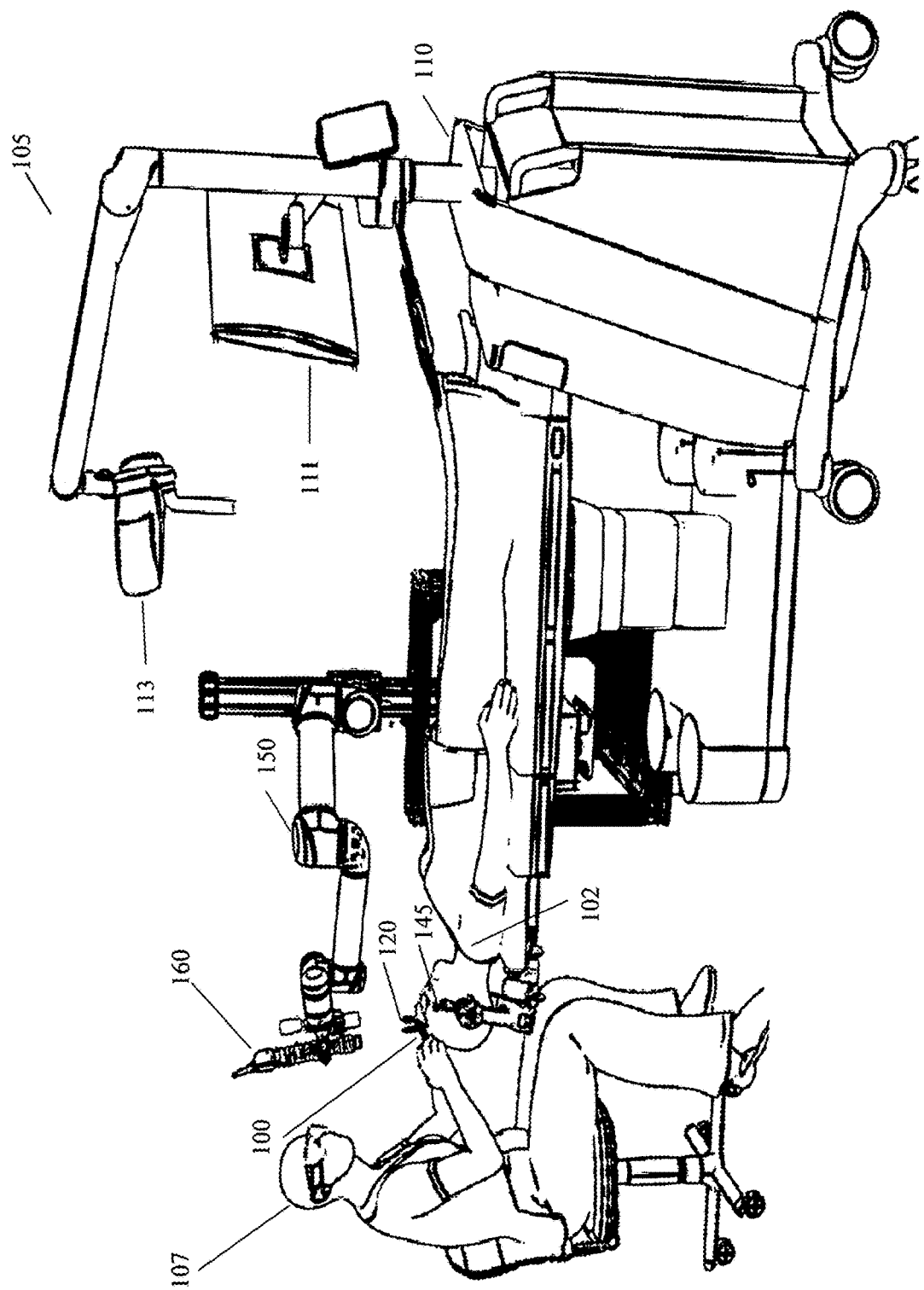
FIG. 1 illustrates systems and equipment of an exemplary neurosurgical procedure in accordance with example embodiments of the present disclosure.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. Unless otherwise specified, the terms "about" and "approximately" mean plus or minus 25 percent or less.

It is to be understood that unless otherwise specified, any specified range or group is as a shorthand way of referring to each and every member of a range or group individually, as well as each and every possible sub-range or sub-group encompassed therein and similarly with respect to any sub-ranges or sub-groups therein. Unless otherwise specified, the present disclosure relates to and explicitly incorporates each and every specific member and combination of sub-ranges or sub-groups.

As used herein, the term "on the order of", when used in conjunction with a quantity or parameter, refers to a range spanning approximately one tenth to ten times the stated quantity or parameter.

Unless defined otherwise, all technical and scientific terms used herein are intended to have the same meaning as commonly understood to one of ordinary skill in the art.

Unless otherwise indicated, such as through context, as used herein, the following terms are intended to have the following meanings:

As used herein, the phrase "access corridor" or "access port" refers to a cannula, conduit, sheath, port, tube, or other structure that is insertable into a subject, in order to provide access to internal tissue, organs, or other biological substances. In some embodiments, an access port may directly expose internal tissue, for example, via an opening or aperture at a distal end thereof, and/or via an opening or aperture at an intermediate location along a length thereof. In other embodiments, an access port may provide indirect access, via one or more surfaces that are transparent, or partially transparent, to one or more forms of energy or radiation, such as, but not limited to, electromagnetic waves and acoustic waves.

As used herein, the phrase "intraoperative" refers to an action, process, method, event or step that occurs or is carried out during at least a portion of a medical procedure. Intraoperative, as defined herein, is not limited to surgical procedures, and may refer to other types of medical procedures, such as diagnostic and therapeutic procedures.

As used herein, the phrase "navigation system" refers to a system that assists in surgery by providing previously acquired imaging information during surgery to visualize tissue morphology and locate target areas. Navigation systems may also be used to track surgical instruments and their location within the tissue during surgery, typically incorporating information from previously acquired imaging data.

As used herein, the phrase "positional tracking system" refers to a computer-implemented system that tracks the position of surgical instruments during surgery. A positional tracking system may be incorporated in a navigation system or may function independently of a navigation system. Where embodiments of the present disclosure refer to a navigation system, an independent positional tracking system may be alternately used.

Embodiments of the present disclosure provide suction devices that are insertable into a subject or patient for manipulation of internal tissues, and methods of use thereof. Some embodiments of the present disclosure relate to minimally invasive medical procedures that are performed via an access port, whereby surgery, diagnostic imaging, therapy, or other medical procedures are performed based on access to internal tissue through the access port.

Several embodiments of the present disclosure seek to address the aforementioned inadequacies of existing devices and methods to support surgical procedures utilizing surgical tools.

Figure 2:
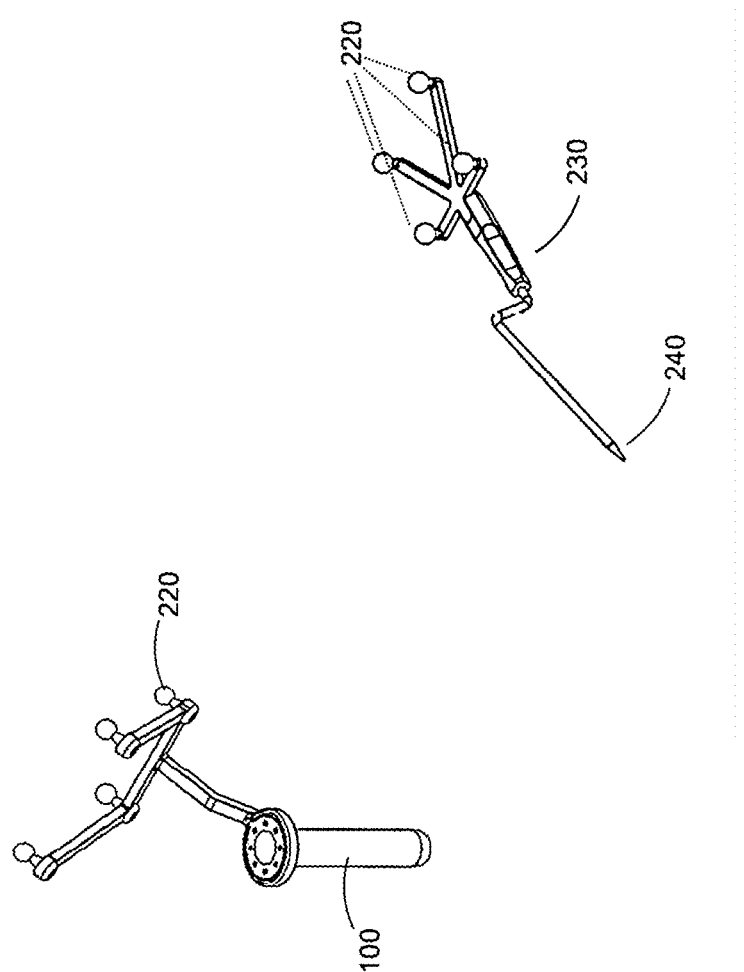
FIG. 2 illustrates exemplary tracked instruments in accordance with example embodiments of the present disclosure.

Minimally invasive brain surgery using access ports is a method of performing surgery on brain tumors previously considered inoperable. One object of the present invention is to provide a system and method to assist in minimally invasive brain surgery. To address intracranial surgical concerns, navigation systems and robotic positioning systems have been developed for port-based surgery. Referring to FIG. 1 and FIG. 2, port 100 comprises of a cylindrical assembly formed of an outer sheath. Port 100 may accommodate an introducer which is an internal cylinder that slidably engages the internal surface of port 100. The introducer may have a distal end in the form of a conical atraumatic tip to allow for insertion into the sulcal folds of the brain. Port 100 has a sufficient diameter to enable bimanual manipulation of surgical tools within its annular opening such as suctioning devices, scissors, scalpels, and cutting devices as examples.

Surgical Positional Tracking System

Surgical positional tracking systems are computer-implemented systems that track the position of surgical tools, such tools including but not limited to access corridors, pointers and suction devices. Positional tracking systems may track the location of surgical tools with respect to a patient and may be used in conjunction with medical images of the patient and site of surgery. An example of a surgical positional tracking system is a navigation system, as described below.

The description below makes reference to the brain of a patient 102 as an example of tissue to which the techniques herein may be applied. It will be understood, however, that those techniques may also be applied to a wide variety of other tissues. Thus, when the brain of patient 102 is mentioned below, it is simply an example of the various tissues in connection with which the systems and methods herein may be implemented. In particular, suction tools are widely used in surgery, thus a tracked suction device will be useful in virtually all types of navigated procedures. Other examples of navigated procedures wherein a tracked suction device would be useful are spine, ENT (ear nose throat), orthopedic and cardiac surgery.

FIG. 1 illustrates systems and equipment of an exemplary neurosurgical procedure. Referring to FIG. 1, an exemplary navigation system 105 which may be used in surgery is shown. A surgeon 107 conducts a surgery on a patient 102 in an operating room environment. The medical navigation system 105 is illustrated including an equipment tower 110, supporting a computing device (not shown) such as a desktop computer, as well as one or more displays 111 connected to the computing device for displaying images provided by the computing device.

Equipment tower 110 also supports a tracking system 113. Tracking system 113 is generally configured to track the positions of one or more tracking markers 120 mounted on access port 100, or any of the above-mentioned surgical tools, or any combination thereof. Such markers may also be mounted on patient 102, for example at various points on the head 145 of patient 102. Tracking system 113 may therefore include a camera (e.g. a stereo camera) and a computing device (either the same device as mentioned above or a separate device) configured to locate the tracking markers in the images captured by the camera, and determine the spatial positions of those markers within the operating theatre. The spatial positions may be provided by tracking system 113 to the computing device in equipment tower 110 for subsequent use.

The nature of the markers and the camera are not particularly limited. For example, the camera may be sensitive to infrared (IR) light, and tracking system 113 may include one or more IR emitters (e.g. IR light emitting diodes (LEDs)) to shine IR light on the markers. In other examples, marker recognition in tracking system 113 may be based on radio frequency (RF) radiation, visible light emitted from devices such as pulsed or un-pulsed LEDs, electromagnetic radiation other than IR or visible light, and the like. For RF and electro-magnetic (EM)-based tracking, each object can be fitted with markers having signatures unique to that object, and tracking system 113 can include antennae rather than the above mentioned camera. Combinations of the above may also be employed.

Each tracked object generally includes three or more markers fixed at predefined locations on the object. The predefined locations, as well as the geometry of each tracked object, are configured within tracking system 113, and thus tracking system 113 is configured to image the operating theatre, compare the positions of any visible markers to the pre-configured geometry and marker locations, and based on the comparison, determine which tracked objects are present in the field of view of the camera, as well as what positions those objects are currently in.

Also shown in FIG. 1 is an automated articulated arm 150, also referred to as a robotic arm or a positioning arm, carrying an external scope 160 (i.e. external to patient 102). External scope 160 may be positioned over access port 100 by robotic arm 150, and may capture images of the brain of patient 102 for presentation on display 111. The movement of robotic arm 150 to place external scope 160 correctly over access port 100 may be guided by tracking system 113 and the computing device in equipment tr 110. The images from external scope 160 presented on display 111 may be overlaid with other images, including images obtained prior to the surgical procedure. The images presented on display 111 may also display virtual models of surgical instruments present in the field of view of tracking system 113 (the positions and orientations of the models having been determined by tracking system 113 from the positions of the markers mentioned above). Alternatively, a tracking camera may be affixed to a monitor or camera cart and connected directly to a positional tracking system, which receives the tracking camera information and analyzes it.

Tracking Markers

FIG. 2 illustrates exemplary tracked instruments with which aspects of the present application may be applied. Referring to FIG. 2, active or passive tracking markers 220 may be placed on the port 100 and/or any medical instruments 230 to determine the location of these objects using the tracking system 113 and navigation system 105. These markers 220 may be passive reflective spheres configured to be seen by the stereo camera of the tracking system 113 to provide identifiable points for tracking. A tracked instrument in the tracking system is typically defined by a grouping of markers 220, which are used to determine the spatial position and pose of the volume of the tracked instrument in three dimensions. Typically, in known exemplary tracking systems a minimum of three spheres are required on a tracked tool to define the instrument.

In a preferred embodiment, the navigation system 105 or positional tracking system may utilize reflective sphere markers in combination with a stereo camera system, to determine spatial positioning and pose of the medical instruments and other objects within the operating theater. Differentiation of the types of objects and their corresponding virtual geometric volumes may be determined by the specific orientation of the reflective spheres relative to one another giving each virtual object an individual identity within the navigation system 105 or positional tracking system. This allows the navigation system 105 or positional tracking system to identify the medical instrument 230 or other object and its corresponding virtual overlay representation. The location of the markers also provides other useful information to the navigation system 105 or positional tracking system, such as the object's central point, central axis, orientation, and other information related to the object.

Trackable Suction Tool

Referring to FIG. 3, an example embodiment of a suction tool 300 that may be tracked during surgical procedures is shown. The suction tool 300 is shown assembled in the left panel and exploded in the right panel. A hollow substantially cylindrical handle 310 includes a main tube 315 with a first proximal end 320 and a distal end 330. The main tube 315 of the handle 310 has an entrance tube 335 extending from the main tube 315 to a second proximal end 337. The main tube 315 and the entrance tube 335 extending from the main tube 315 may form a Y-shaped handle.

The handle includes a tapered elongated slot 340, such as a tear-shaped orifice in the wall of the handle, which is widest at the proximal end and narrowest at the distal end, for controlling the amount of suction provided at the distal end of the suction tool tip. In a preferred embodiment, the handle 310 has a flattened portion 345 around the elongated slot 340, and the flattened portion lies in the plane defined by the main tube 315 and the entrance tube 335.

The handle distal end 330 includes splines and a thread for connection to a tip, as described in further detail below. The handle first proximal end 320 and second proximal end 337 both include ribs for connection to a suction tube and splines and a thread for connection to a tracking mechanism.

The handle distal end 330 is connected to a proximal end 350 of a tubular hollow tip 360. The tip proximal end 350 has splines that are complementary and interlock with the splines on the handle distal end 330, thus providing specific rotational angles of the tip 360 relative to the plane of the handle 310. The connection is secured by a semi-captive nut 365.

A tracking mechanism 370, such as a reference tree, is attached to the first proximal end 320 or second proximal end 337 of the handle 310. The tracking mechanism 370 includes tracking markers, such as reflective sphere markers. The tracking mechanism 370 has splines complementary to the splines on the first and second proximal ends of the handle, providing fixed rotational positions of the tree relative to the plane of the handle 310 defined by the main tube 315 and the entrance tube 335. The attachment of the tracking mechanism 370 to the handle 310 is secured with a captive nut 375. A suction tube (not shown) may be attached to the first or second proximal end 320, 337 of the handle 310 by sliding the suction tube over the ribs 377.

The handle 310 can be used to hold and manipulate the suction tool 300, such that the tip distal end 380 is directed to the tissue, for example for holding or resecting tissue or suctioning fluids. The tip distal end 380 is also blunted to minimize trauma to tissue while in use. The tracking mechanism 370 provides an optical marker for tracking the position of the suction tool 300 and provides position information to the tracking system 113.

The tip 360 can be removed from the handle 310 by rotating and unscrewing the semi-captive nut 365 until it is released from the threads of the distal end of the handle 330; tips of different configurations can thereby be exchanged and used with the suction tool. The tip 360 may be one of several different lengths, angles and diameters. Thus, by removing and replacing the tip 360, the suction tool may have different configurations. Information on the parameters for a given tip, such as tip length, diameter and angle, can be entered and stored by the computing device of the navigation system 105, and calibrated using the calibration apparatus (as described for FIG. 10), so that for each tip 360 used with the suction tool 300, the position of the tip distal end 380 is accurately tracked.

Tip Attachment Mechanism

Figure 4:
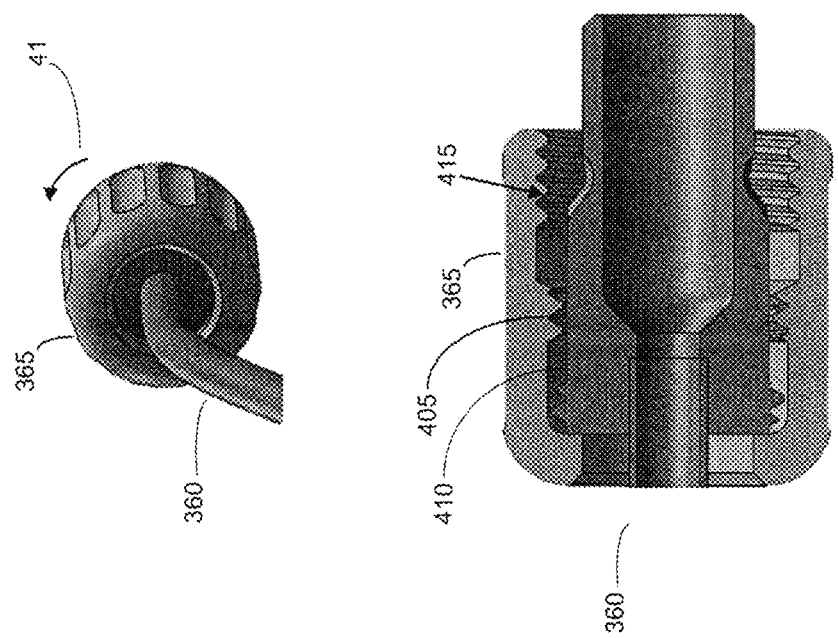
FIG. 4 illustrates a perspective and cross-sectional view of an attachment mechanism for attaching a tip to a handle in accordance with example embodiments of the present disclosure.

Referring to FIG. 4, a perspective view of the tip 360 and semi-captive nut 365 is shown in the top panel and a cross-sectional view of the nut 365 threaded onto the tip 360 is shown in the lower panel.

The semi-captive nut 365 has two internal threads: a left-hand and a right-hand thread. In the embodiment shown, a left-hand internal thread 405 engages the nut 365 onto the tip 360 to prevent the nut from slipping off the tip during assembly and disassembly of the tip onto the handle. The nut seating position 410 provides free rotation of the nut 365 around the tip 360 without removing the nut from the tip. A larger diameter right-hand internal thread 415 is used to secure the tip 360 to the handle (not shown).

Figure 5:
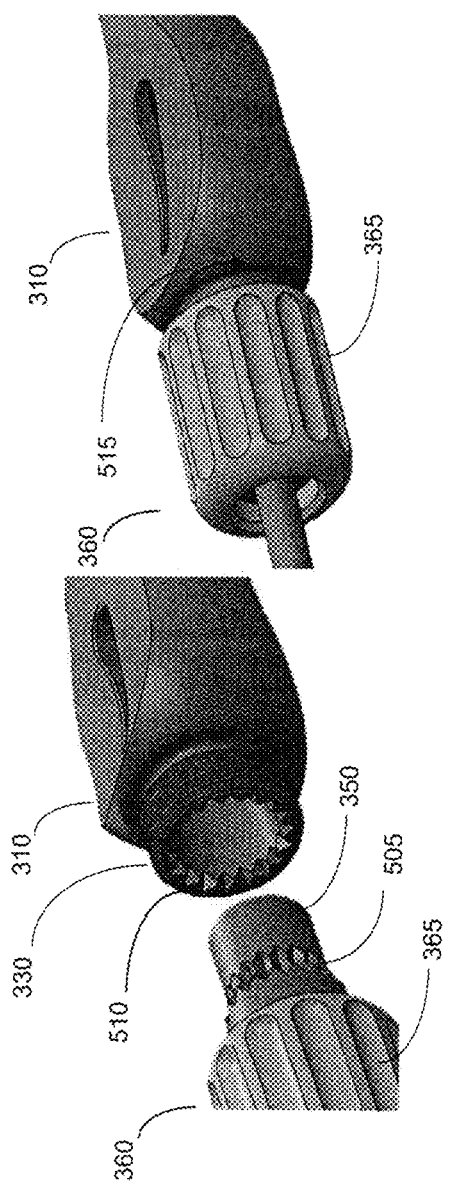
FIG. 5 further illustrates an attachment mechanism for attaching a tip to a handle in accordance with example embodiments of the present disclosure.

Referring to FIG. 5 a perspective view of the attachment mechanism for the tip 360 to the handle 310 is shown in the left panel and the secured tip and handle are shown in the right panel. External splines 505 on the tip proximal end 350 are complementary to internal splines 510 on the handle distal end 330. The tip external splines 505 fit into the handle internal splines 510 to prevent rotation and hold the tip at a fixed position after securing the tip with the nut 365. In an embodiment, the tip and handle ends have 18 splines, allowing for 18 rotational positions (20° apart) of the tip around the axis of the handle.

Further referring to FIG. 4 and FIG. 5, to attach the tip to the handle, the semi-captive nut 365 is slid onto the tip 360 until the internal left-hand thread 405 is engaged with the thread on the tip proximal end 350. The nut 365 is threaded onto the tip 360 until the tip threads sit in the seating position 410, so the nut is attached to the tip but able to freely rotate. The tip 360 is then inserted into the handle 310 fully to mate the internal 510 and external splines 505. The nut 365 is then threaded in the opposite direction 515 onto the handle distal end 330 until the tip 360 is fully seated and secured.

Tube and Tracking Mechanism Attachment

Referring to FIG. 6, a perspective and side view of the fittings for attaching the suction tube or hose or the tracking mechanism, such as a reference tree, to the handle are shown. The first and second proximal ends 320, 337 of the handle 310 both include ribs 377 for attachment of a suction tube (not shown in FIG. 6) and adjacent threads 610 for a tracking device nut. The tube is attached up to the start of the threads for smaller tube diameters and, as shown in FIG. 7, the tube 705 is attached over the threads 610 for larger tube diameters.

Figure 8:
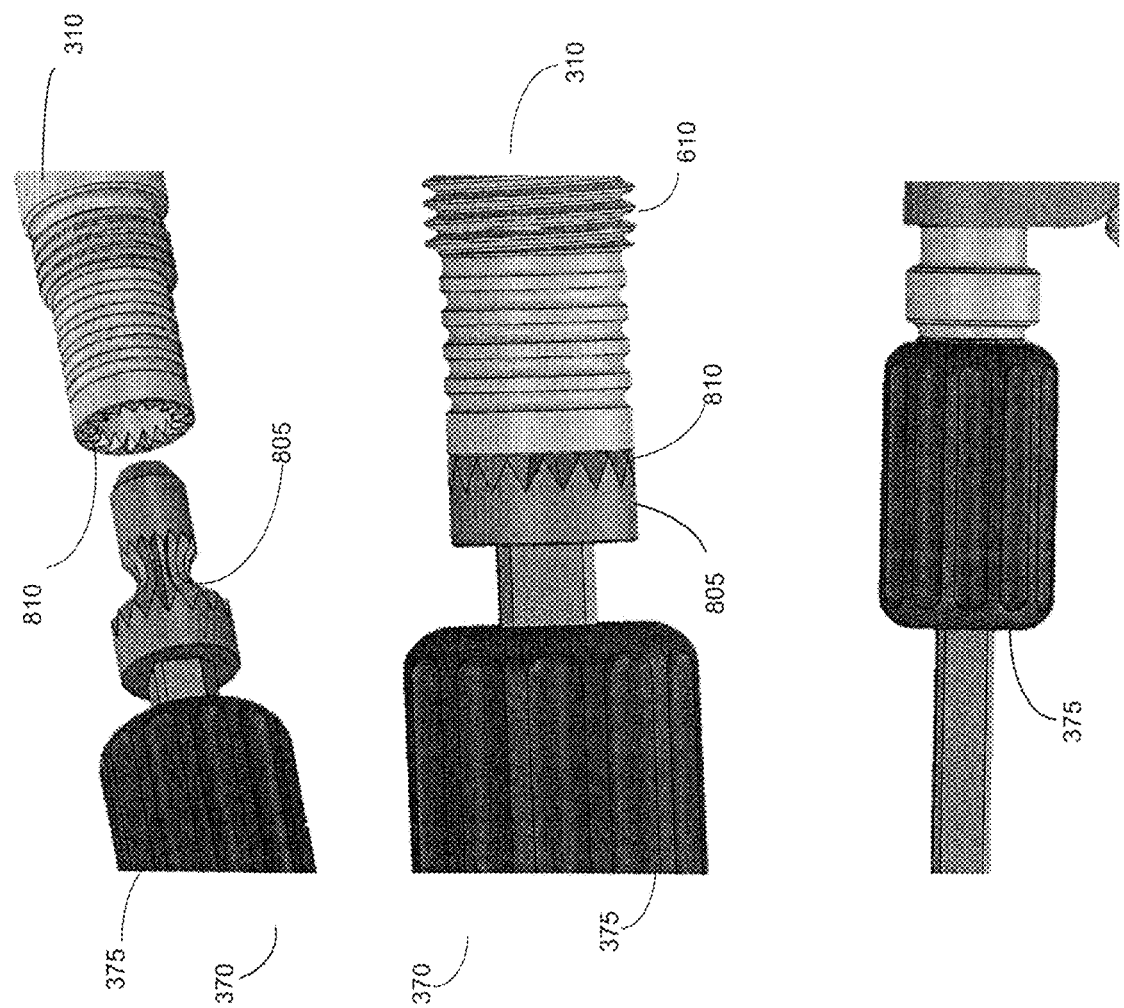
FIG. 8 illustrates an attachment mechanism for attaching a handle to a tracking device in accordance with example embodiments of the present disclosure.

Referring to FIG. 8, attachment fittings for a tracking mechanism, such as a reference tree, 370 at the first or second proximal end of the handle 310 is shown. The top panel of FIG. 8 illustrates an unattached tracking mechanism 370 and handle 310. The tracking mechanism end has splines 805 that fit into complementary splines 810 on the handle proximal end, which prevent rotation after the tracking mechanism is secured with the captive nut 375. In an embodiment, the tracking mechanism includes 16 external splines and the handle includes 16 internal splines, thereby allowing 16 rotational positions, 22.5° apart, to maximize flexibility with the tool positioning relative to the camera of the navigational system. The middle panel of FIG. 8 illustrates the tracking mechanism 370 and handle 310 with fully seated splines 805, 810 prior to threading the captive nut 375 onto the threads 610, and the lower panel of FIG. 8 illustrates the tracking mechanism and handle fully secured with the captive nut 375 screwed onto the threads.

Referring back to FIG. 3, the attachment mechanisms as described provide for multiple positions of the tip 360 relative to the tracking mechanism 370 around the circumference of the handle 310, allowing easier use for right and left hand users and for different positions of an angled tip without obstructing the line of sight for the tracking mechanism 370. Multiple positions of the tracking mechanism 370 are also enabled by placement on either the first or second proximal end of the handle 320, 337, and by rotating the tracking mechanism position relative to the handle by locking into different spline positions. The rotatable tracking mechanism 370 affords rotation of the tracking mechanism to optimize line of sight and provide a preferred working configuration, while maintaining a fixed rotational axis of the tracking mechanism 370 relative to the plane of the handle defined by the handle main tube 315 and entrance tube 335. The attachment mechanisms also allow different tracking mechanism 370 configurations to be switched out for unique identification of one or more suction tools/medical instruments in the same surgical space.

Figure 9:
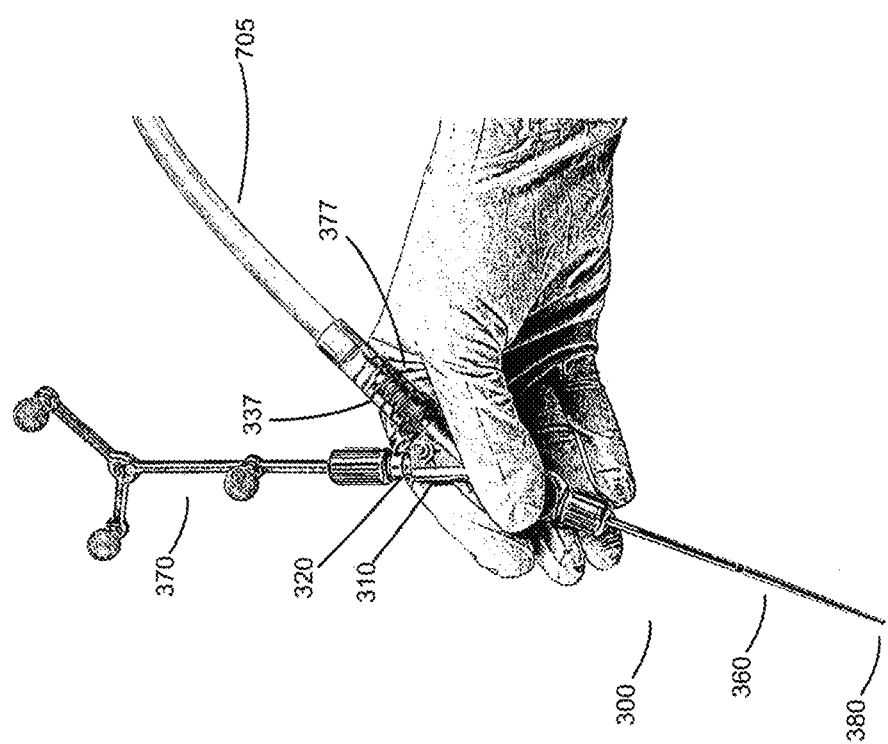
FIG. 9 illustrates use of a tracked suction device in accordance with example embodiments of the present disclosure.

FIG. 9 illustrates a tracked suction tool held in the hand of a user. Referring to FIG. 9, a suction tool 300, such as that illustrated in FIG. 3, is held by user (i.e., a surgeon), with the tracking markers of the tracking mechanism 370 providing positional information of the suction tool 300 to the tracking system 113 (FIG. 1), so the positional tracking system or navigation system 105 (FIG. 1) is able to calculate and display the position of the suction tool tip 360 to the surgeon. Suction tool 300 is connected to suction tube 705 at the handle first or second proximal end 320, 337. The rib aspect 377 of handle proximal ends 320, 337 ensures for a tight and secure fit with suction tube 705.

The suction tool 300 is registered in the positional tracking system or navigation system 105 (FIG. 1) and prior to use is calibrated to provide accurate registration of the tracking markers 220 (FIG. 2) with the tip distal end 380. Calibration ensures that a current configuration of the suction tool 300 is accurately registered in the positional tracking system or navigation system 105 (FIG. 1), including changes such as different tips, adjustment of the tracking mechanism 370, user's grip of the suction tool, and deformations of the tip 360. A vacuum tube or suction tube 705 is shown connected to the proximal end 320, 337 of the handle 310.

As seen in FIGS. 3 to 9, the suction tool 300 is equipped with an exchangeable hollow tip 360. The tip may include a bend between the proximal end and distal end. The bend angle may range between 60 and 180 degrees. The tip 360 may also be rigid or malleable. A rigid tip is distinguished from a malleable tip by an external marking to enable the surgeon to easily distinguish them. The malleable tip can be further bent by the user (surgeon) during the medical procedure.

The hollow tip may range in length between 50 mm and 250 mm in length and may have a diameter between 3 and 34 FR.

The above embodiments allow a choice of which hand to use to hold the suction tool, specific holding angles to be attained, the reference tree to be manipulated for the best view, and allow suction tools to be customized and replaced with accuracy and minimum inconvenience.

Calibration of Tracked Medical Instrument

In order to provide the dimensions of the tracked suction tool 300, the dimensions of the tracked suction tool may be registered and stored in the navigation system 105 or positional tracking system, and subsequently calibrated before use in surgery using procedures known in the art. An exemplary calibration procedure is provided below.

Referring to FIG. 10, a a tracked suction tool 310 is shown with a calibration apparatus 1010. The techniques for calibrating a tracked instrument can be found in international application CA2014051004 titled "CALIBRATION APPARATUS FOR A MEDICAL TOOL" which is incorporated by reference herein in its entirety.

The suction tool 300 and the calibration apparatus 1010 are typically used in conjunction with a positional tracking system, such as the medical navigation system 105. The calibration apparatus 1010 includes a frame 1020, at least one frame tracking marker 1030 attached to the frame 1020, and a reference point 1040 formed on the frame 1020. In one example, the reference point 1040 may be a divot that is of an appropriate shape for securely receiving the distal end of the suction tool tip 380. For the purposes of this example, the reference point 1040 will be referred to throughout as a divot 1040. The divot 1040 may provide a known spatial reference point relative to the frame tracking markers 1030. For example, the medical navigation system 105 may have data saved therein so that the medical navigation system knows the position in space of a floor of the divot 1040 relative to the tracking markers 1030 to a high degree of accuracy. In one example, a high degree of accuracy may refer to a tolerance of 0.08 mm, but any suitable tolerance may be used according to the design criteria of a particular application.

In the example shown, the calibration apparatus 1010 has four passive reflective tracking spheres, but any suitable number of tracking markers 1030 may be used and any suitable type of tracking marker may be used according to the design criteria of a particular application, including an active infrared (IR) marker, an active light emitting diode (LED), and a graphical pattern. When passive reflective tracking spheres are used as the tracking makers 1030, typically at least three tracking markers will be attached to a same side of the frame 1020. Likewise, when a suction tool 300 having passive reflective tracking spheres is used in conjunction with the calibration apparatus 1010, the suction tool will typically have at least three tracking markers 220 attached thereto.

Referring to FIG. 10, left panel, the distal end 380 of the suction tool 300 is inserted into the calibration apparatus 1010 for a reading by the medical navigation system 105. When the suction tool 300 is inserted into the calibration apparatus 1010, the position of the distal end 380 of the suction tool 300 relative to the tracking markers 220 that the medical navigation system 105 is seeing (e.g., using the camera of the tracking system 113) may be learned and saved by the navigation system 105. The distal end 380 of the suction tool 300 is then inserted onto the divot 1040 for verification of the localization of the suction tool 300. Since the medical navigation system 105 knows the precise dimensions of the calibration apparatus 1010, the medical navigation system 105 learns the dimensions of the suction tool 300. In other words, the position of the floor of the divot 1040 relative to the tracking markers 220 that the medical navigation system 105 is seeing (e.g., using the camera of the tracking system 113) is known. Other calibration devices and methods may be used to localize the distal end 380 of the suction tool 300 relative to the tracking markers 220.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

We claim:

1. A tracked suction device for use in a medical procedure comprising:
    an elongated tubular handle with a central passage, a main tube having a first proximal end, a distal end, and a flattened section with a suction-regulating orifice communicating with the central passage, and an entrance tube extending from the main tube having a second proximal end;
    an elongated tip, having a hollow tubular body, a tip distal end, and a tip proximal end detachably connected to the main tube distal end with a tip attachment mechanism that provides a plurality of fixed positions of the tip relative to the handle, the tip attachment mechanism comprising a threaded ring and splines; and a reference tree for tracking the tip distal end, the reference tree detachably connected to the handle first or second proximal end, wherein the reference tree is attached to the handle with a reference tree attachment mechanism that provides a plurality of fixed positions of the reference tree relative to the handle, the reference tree attachment mechanism comprising a threaded ring and splines;

wherein the flattened section of the main tube lies in a plane defined by the main tube and the entrance tube, and the handle first and second proximal ends each have threads to attach the reference tree and ribs to attach the suction tube.

2. The device as in claim 1, wherein the entrance tube extends from the main tube at less than 90°.

3. The device as in claim 1, wherein the orifice in the handle is a tear-shaped orifice.

4. The device as in claim 1, wherein the tip attachment mechanism further comprises complementary splines on the handle and the tip proximal end.

5. The device as in claim 1, wherein the tip attachment mechanism further comprises a threaded semi-captive nut to attach the tip proximal end to the handle, wherein the threaded semi-captive nut comprises a first internal thread to engage the tip proximal end, a nut seating position to provide free rotation of the nut when the nut is engaged with the tip proximal end through the first internal thread, and a second internal thread with a larger diameter than the first internal thread to engage the handle.

6. The device as in claim 1, wherein the reference tree attachment mechanism further comprises complementary splines on the handle and the reference tree.

7. The device as in claim 1, wherein the reference tree attachment mechanism further comprises a threaded captive nut to attach the reference tree to the handle.

8. The device as in claim 1, wherein the reference tree comprises markers for an optical navigation system.

\* \* \* \* \*